United States Patent
Martin

(10) Patent No.: US 9,656,891 B2
(45) Date of Patent: May 23, 2017

(54) CHLORINE DIOXIDE GENERATOR FOR THE EFFICIENT GENERATION OF CHLORINE DIOXIDE IN DILUTE SOLUTIONS

(71) Applicant: Roy W. Martin, Downers Grove, IL (US)

(72) Inventor: Roy W. Martin, Downers Grove, IL (US)

(73) Assignee: TRUOX, INC., McClellan, CA (US)

( * ) Notice: Subject to any disclaimer, the term of this patent is extended or adjusted under 35 U.S.C. 154(b) by 267 days.

(21) Appl. No.: 14/121,322

(22) Filed: Aug. 20, 2014

(65) Prior Publication Data

US 2015/0065403 A1    Mar. 5, 2015

Related U.S. Application Data

(63) Continuation-in-part of application No. 13/987,793, filed on Sep. 3, 2013, now abandoned.

(51) Int. Cl.
| | |
|---|---|
| C02F 1/76 | (2006.01) |
| C02F 1/68 | (2006.01) |
| C09K 8/66 | (2006.01) |
| A01N 59/00 | (2006.01) |
| C09K 8/60 | (2006.01) |
| C02F 103/02 | (2006.01) |
| C02F 103/10 | (2006.01) |
| C02F 103/36 | (2006.01) |

(52) U.S. Cl.
CPC .............. *C02F 1/76* (2013.01); *A01N 59/00* (2013.01); *C02F 1/68* (2013.01); *C09K 8/605* (2013.01); *C09K 8/665* (2013.01); *C02F 2103/023* (2013.01); *C02F 2103/10* (2013.01); *C02F 2103/365* (2013.01); *C02F 2209/003* (2013.01); *C02F 2209/04* (2013.01); *C02F 2209/06* (2013.01); *C02F 2209/29* (2013.01); *C02F 2209/40* (2013.01)

(58) Field of Classification Search
USPC .......................................................... 423/477
See application file for complete search history.

(56) References Cited

U.S. PATENT DOCUMENTS

| | | | |
|---|---|---|---|
| 6,855,294 | B2 | 2/2005 | Taylor |
| 7,311,884 | B2 | 12/2007 | Brownfield et al. |
| 7,407,641 | B2 | 8/2008 | Cowley et al. |
| 7,504,074 | B2 | 3/2009 | Martens et al. |
| 7,754,057 | B2 | 7/2010 | O'leary et al. |
| 7,833,392 | B2 | 11/2010 | Nanjundiah et al. |
| 7,964,138 | B2 | 6/2011 | Richardson et al. |
| 8,211,296 | B2 | 7/2012 | Angelilli et al. |
| 2005/0244328 | A1* | 11/2005 | Schmitz .................... A61L 2/20 423/477 |
| 2006/0034750 | A1* | 2/2006 | Lee ...................... B01J 19/0013 423/477 |

(Continued)

*Primary Examiner* — Chester Barry

(57) ABSTRACT

Disclosed is a process for the safe and efficient generation of chlorine dioxide while achieving a variable chlorine dioxide mass flow rate with a turn-down to turn-up ratio of at least 1 to 200. The process allows for a single chlorine dioxide generating system to safely provide variable mass flow rate of chlorine dioxide to applications that have wide ranging chlorine dioxide demand, like those experienced in oil and gas applications.

9 Claims, 1 Drawing Sheet

(56) References Cited

U.S. PATENT DOCUMENTS

| | | | |
|---|---|---|---|
| 2008/0152580 A1* | 6/2008 | Simpson | B01F 3/0446 423/477 |
| 2014/0072656 A1* | 3/2014 | Mitchell | C02F 1/76 424/661 |
| 2015/0065403 A1* | 3/2015 | Martin | C02F 1/76 507/269 |

* cited by examiner

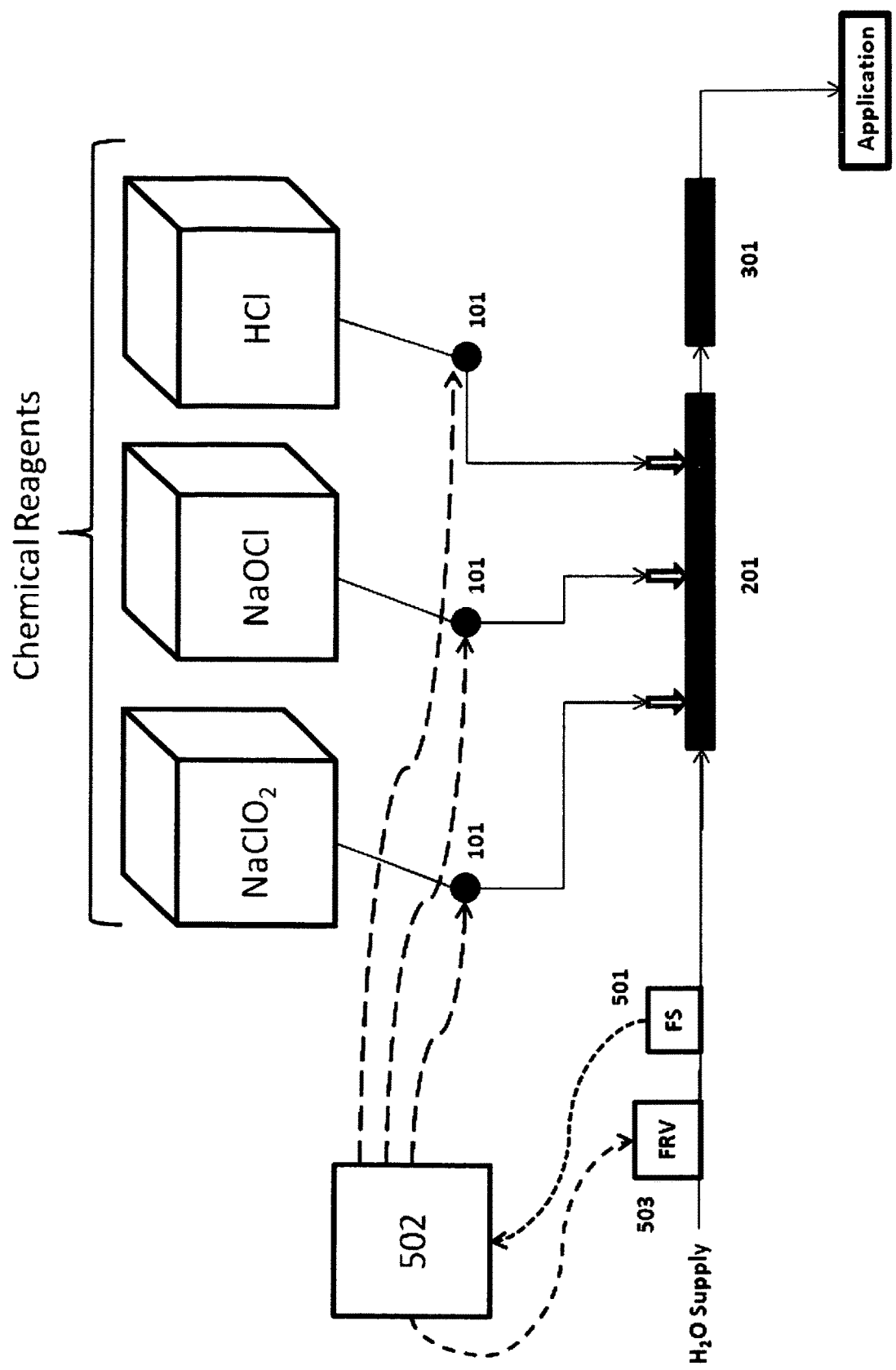

CHLORINE DIOXIDE GENERATOR FOR THE EFFICIENT GENERATION OF CHLORINE DIOXIDE IN DILUTE SOLUTIONS

CROSS-REFERENCE TO RELATED APPLICATIONS

This application is a Continuation-In-Part of application Ser. No. 13/987,793 filed Sep. 3, 2013, which is a continuation of Provisional Application No. 61/743,436 filed on Sep. 4, 2012. The priority applications ale expressly incorporated by reference.

BRIEF DESCRIPTION

Chlorine dioxide generators come in a variety of configurations and use a range of generating techniques. Generators that use chlorite, hypochlorite, and acid often comprise an eductor to form a vacuum to extract a highly concentrated stream of chlorine dioxide gas and dilute it with water to produce a chlorine dioxide solution. Another prior art method is to predetermine a concentration of chlorine dioxide and adjusting the dilution water flow rate to deliver the generated chlorine dioxide at the desired mass flow rate to achieve the target treatment concentration in the treated process.

Eductor based apparatus have the potential to cause explosion and/or significant harm to personnel due to contact with highly concentrated chlorine dioxide in the event of a malfunction. Variable dilution water flow rates greatly limit the ability to treat process stream that experience variances in process flow rate as chlorine dioxide demand.

The invention provides an automated process for producing variable mass flow rates of dilute chlorine dioxide solution with a turn-down turn-up ratio ranging from at least 1 to 200, while providing a concentration of chlorine dioxide exiting the generator ranging from 50 ppm to 5000 ppm as chlorine dioxide, more preferably 100 ppm to 4000 ppm as chlorine dioxide, and most preferred 100 ppm to 3000 ppm as chlorine dioxide. The invention provides for greater flexibility that is required for treating applications such as those experienced in oil and gas applications such as treating hydraulic fracturing water where process flow rates and chlorine dioxide demand can vary greatly in relatively short periods of time.

The invention provides for the safe and efficient generation of chlorine dioxide with at least 80 wt %, more preferably at least 90 wt %, and most preferably at least 95 wt % conversion of chlorite anion to chlorine dioxide without the need of forming concentrated streams of chlorine dioxide prior to dilution with water.

DEFINITIONS

As used herein, "turn-down turn-up ratio" describes the variability in the mass flow rate of chlorine dioxide exiting the chlorine dioxide generator. The chlorine dioxide generator can vary the mass flow rate of chlorine dioxide by adjusting the concentration (mg/liter) of chlorine dioxide for a targeted motive water flow rate by adjusting the feed rate of the chemical pumps to achieve from 50 to 5000 ppm (mg/liter) as $ClO_2$. If greater mass flow rate of chlorine dioxide is desired the PLC in signal control with the flow regulating valve can increased the motive water flow rate, thereby reducing the concentration of chlorine dioxide leaving the generator at the same mass flow rate. Once the concentration of chlorine dioxide leaving the generator is below the maximum $ClO_2$ set-point by some predetermined value (e.g. 10%), the PLC then increases the feed rate of the chemical pumps to further increase the chlorine dioxide concentration, thereby increasing the mass flow rate of chlorine dioxide without compromising safety. The process disclosed provides a turn-down turn-up ratio of at least 1 to 200, preferably at least 1 to 300, and most preferably at least 1 to 500. Mass flow rate can be measured or reported in any convenient manner illustrated by the non-limiting examples: mg/min, g/min, g/hr, lbs/hr and the like.

As used herein, "turn-down turn-up logic" describes the logic within the PLC that controls the chemical feed rate and motive water flow rate to not exceed the maximum $ClO_2$ set-point (concentration in mg/l) of chlorine dioxide exiting the generator while allowing increased or decreased mass flow rate of chlorine dioxide exiting the generator. In this illustrative example, the turn-down turn-up logic: monitors either calculated and/or measured chlorine dioxide concentrations exiting the generator to a predetermined maximum $ClO_2$ set-point, limits the feed rate of chemicals for generating chlorine dioxide as to not exceed the maximum $ClO_2$ set-point of chlorine dioxide exiting the generator, increases the motive water flow rate by adjusting the flow regulating valve by some increment allowing more water to flow thru the chlorine dioxide generator, confirms the calculated and/or measured chlorine dioxide concentration is less than the maximum $ClO_2$ set-point, then increases the feed rate of the chemicals to increase the mass flow rate of chlorine dioxide exiting the generator. The motive flow rate can be adjusted based on the proportional increase in mass flow rate of chlorine dioxide required to meet the demands of the application, but it is preferably adjusted based on a predetermined percentage (i.e. 10% or 20%) to allow for additional safety and smaller increments of adjustments to the chemical feed rates without need for additional motive flow rate adjustment. The same logic can be used to decrease the motive flow rate if a minimum $ClO_2$ set-point is reached. For example, if the minimum set-point is set at 50 mg/l and it is reached, the PLC can begin closing the flow regulating valve to increase the concentration of chlorine dioxide in the motive water exiting the generator to provide for faster reaction times.

As used herein, "safe and efficient generation of chlorine dioxide" describes the invention's ability to produce chlorine dioxide with high conversion of chlorite anion to chlorine dioxide without producing a process stream of chlorine dioxide that has a concentration of chlorine dioxide gas that is potentially explosive. The term "safe" refers to the inventions inherent safe generation of chlorine dioxide achieved by diluting a source of chlorite in water to achieve a concentration of chlorite anion necessary to provide less than or equal to 5000 ppm chlorine dioxide in a reaction zone that is flooded with water.

The flooded reaction zone is the result of the control panel confirming motive water has been measured flowing thru the variable mass flow rate chlorine dioxide generator with a flow rate at or greater than a predetermined value and for a predetermined period of time to ensure the reaction zone and post reactor conduit in fluid contact with the reaction zone are flooded before actuating the chemical feed pumps.

By diluting the source of chlorite before generating chlorine dioxide, at no time is the concentration of chlorine dioxide at explosive levels. The term "efficient" describes the efficient generation of chlorine dioxide resulting from the conversion of chlorite anion (as $ClO_2^-$) to chlorine dioxide ($ClO_2$) of at least 80 wt %, more preferably 90 wt %, and most preferably 95 wt % conversion of chlorite anion to chlorine dioxide. The wt % (weight percent) conversion of chlorite anion to chlorine dioxide can be determined by dividing the parts per million of chlorine dioxide by the parts per million of chlorite anion multiplied by 100. The equation is exemplified by: [$ClO_2$ (ppm)/$ClO_2^-$ (ppm)]×100=wt % conversion of chlorite anion to chlorine dioxide.

As used herein, "dilute aqueous solution of chlorine dioxide" describes the effluent aqueous solution discharged from the reaction chamber having a chlorine dioxide concentration of less than or equal to 5000 ppm measured as $ClO_2$.

As used herein, "flow sensor" describes a device that can detect a liquid flowing through a pipe. The flow sensor can measure, but is not required to measure the flow rate. The flow sensor detects motive water in the pipe. One non-limiting example of a flow sensor is Rotorflow® Flow Sensors available by Gems™ Sensors and Controls.

As used herein, "control panel" describes a system comprising at least a Programmable Logic Controller (PLC) that is in signal contact with devices exemplified by but not limited to variable feed rate chemical pumps and flow regulating valve. Non-limiting examples of other devices comprising the control panel include internally or externally mounted: relays, analog inputs and outputs, digital inputs and outputs, variable frequency drives, flow meters, ORP and pH sensors, optical sensors, and transformers to provide for different power requirements for pumps and sensors.

As used herein, "energize" and "energizing" and its variations describes the activation of an electrical device by closing a circuit that delivers an electrical current to the electrical device so that the electrical device performs a desired function. For example, a flow sensor detects motive water followed by the control panel energizing the chemical feed systems. In contrast, when motive water is no longer confirmed by the flow sensor, the control panel stops the chemical feed systems.

As used herein, "actuated" and "actuating" and its variations is an action initiated by the control panel to cause something to happen such as initiating chemical feed, stopping chemical feed, initiating a flushing cycle and the like.

As used herein, "flushing cycle" describes a process of rinsing at least the injection manifold and reaction chamber with water or a neutralizing solution that neutralizes chlorine dioxide, and acidified chlorine and/or their respective chemical sources exemplified by sodium chlorite, sodium hypochlorite, and hydrochloric acid. One example of a neutralizing solution is a solution of sodium sulfite.

As used herein, "signal contact" describes the ability of an electronic device exemplified by a flow sensor to communicate with the control panel and/or a device exemplified by a flow regulating valve to communicate with and be controlled by the control panel.

As used herein, the term "efficient" describes the capacity of the process to achieve at least 80 wt %, more preferably 90 wt %, and most preferably 95 wt % conversion of chlorite anions to chlorine dioxide. The wt % conversion of chlorite anions to chlorine dioxide can be determined by dividing the parts per million of chlorine dioxide by the parts per million of chlorite anions multiplied by 100. The equation is exemplified by:

[$ClO_2$ (ppm)/$ClO_2^-$ (ppm)]×100=wt % conversion of chlorite anions to chlorine dioxide.

As used herein, "fluid contact" describes intimate contact between conduits capable of transporting liquid between the different conduits.

As used herein, "chemicals for the generation of chlorine dioxide" describes chemicals (reagents) for producing an aqueous solution of acidified chlorine and chlorite anions used to generate a dilute aqueous solution of chlorine dioxide.

As used herein, "source of acidified chlorine" describes reagents needed to produce an aqueous solution of acidified chlorine comprising chlorine gas ($Cl_2$) and/or hypochlorous acid (HOCl). Non-limiting examples of sources of acidified chlorine may comprise a two reagent treatment comprising hydrochloric acid and sodium hypochlorite injected separately into the injection manifold having a source of motive water to form acidified chlorine in-situ, a mixture of a source of chlorine and an acid source injected together into the injection manifold, or a source of chlorine comprising gaseous chlorine that hydrolyzes in the source of motive water to form hydrochloric acid and hypochlorous acid.

As used herein, "injection manifold" describes a manifold with at least two and preferable at least three inlet ports to inject a source of chlorite into a source of motive water separately from the other reagents for the generation of acidified chlorine used to generate chlorine dioxide. One non-limiting example of an injection manifold with two inlet ports injects a source of chlorite into one inlet port and a source of acidified chlorine into the other inlet port. One non-limiting example of a three inlet port manifold injects a source of chlorite, source of chlorine, and an acid source separately through the different inlet ports, wherein the source of chlorine and acid source produce acidified chlorine in-situ.

As used herein, "reaction zone" or "reactor" describes a chamber wherein the aqueous solution comprising water, a source of chlorite, and acidified chlorine react to produce a dilute aqueous solution of chlorine dioxide. Non-limiting examples of a reaction zone include: static mixer, a chamber to increase contact time, or a length of pipe or hose that increases the contact time to provide at least 80 wt % conversion, more preferably at least 90 wt % conversion, and most preferably 95 wt % conversion of chlorite anion to chlorine dioxide. Non-limiting examples of a reaction chamber include: a static mixer, a chamber providing increased volume that increases reactants contact time, and/or a length of pipe or hose that increase the reactants contact time. The reaction chamber improves the efficiency by improving the kinetics through either increasing mixing (e.g. static mixer) and/or the reaction time to allow the reactions to approach completion (increased volume).

As used herein, "source of chlorite" describes a compound that releases chlorite anions having the general formula $ClO_2^-$ when dissolved in water. Non-limiting examples of a source of chlorite include: sodium chlorite, potassium chlorite, and calcium chlorite.

As used herein, "chlorite anion" describes the precursor having the general formula $ClO_2^-$ that is converted into chlorine dioxide $ClO_2$ when reacted with acidified chlorine.

As used herein, "source of chlorine" is any convenient source of chlorine that releases chlorine gas and/or hypochlorous acid when dissolved in an acidified aqueous solution. Non-limiting examples include: gaseous chlorine, sodium hypochlorite, lithium hypochlorite, calcium hypochlorite, dichloroisocyanuric acid, trichloroisocyanuric acid, dichlorodimethyl hydantoin and the like.

As used herein, "acid source" describes any convenient source of a hydrogen ions that reduce the pH when dissolved in water. An acid source can comprise mineral acids and/or organic acids. Non-limiting examples include: hydrochloric acid, phosphoric acid, sulfuric acid, citric acid, tartaric acid, fumaric acid and the like.

As used herein, "variable feed rate chemical pumps" describes chemical feed pumps that can be controlled by a PLC to increase or decrease the chemical feed rate. It is preferred the chemical feed pumps are capability of self-verification of the volume of chemical fed. Some non-limiting examples of variable feed rate chemical pumps include Grundfos DDI and Grundfos DDA chemical feed pumps.

As used herein, "chemical feed systems are slaved together" describes the ability to control the chemical feed-rate in such as way so that altering the output of one chemical (exemplified by the source of chlorite) automatically and proportionally alters the feed-rate of the other chemicals used to generate chlorine dioxide (e.g. acidified chlorine). This proportional slaving of the chemicals feed systems allows for consistent efficiency in the conversion of chlorite anion to chlorine dioxide while providing variability in the production rate of chlorine dioxide. The production rate of chlorine dioxide can be automatically adjusted by the control panel using on feed-back and/or feed-forward control.

As used herein, "variable mass flow rate chlorine dioxide generating system" is a chlorine dioxide generator comprising at least: variable feed rate chemical pumps, chemicals for producing chlorine dioxide, flow meter, flow regulating valve, injection manifold, a reaction zone (reactor), optical sensor for measuring chlorine dioxide concentration exiting the reactor, and sensors in signal contact with the control panel for monitoring process conditions that can influence the mass flow rate of chlorine dioxide exiting the generating system. Non-limiting examples of sensors for determining said process conditions include ORP, chlorine dioxide residual and process water flow rate.

As used herein "process conditions" are the parameters comprising the application being treated with the chlorine dioxide that influence the required mass flow rate of chlorine dioxide exiting the variable mass flow rate chlorine dioxide generating system. Non-limiting examples of process conditions include: process flow rate, process water quality, ORP of the treated process water, chlorine dioxide residual, temperature and the like.

As used herein, "oil and gas applications" comprise water treatment processes for the recovery and production of oil and gas. Examples of water treatment processes for the recovery and production of oil and gas include: hydraulic fracturing, treating of flow-back water, treatment of produced water and treatment of desalination fresh water.

As used herein, the singular forms "a," "an," and "the" Include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

BRIEF DESCRIPTION OF THE FIGURE

The FIGURE shows an embodiment of the invention.

The FIGURE shows flow sensor (501) is in position to detect a source of motive water being supplied to the injection manifold and in signal contact with control panel (502). Control panel (502) is in signal contact with flow regulating valve (503) and in signal contact with the variable feed rate chemical pumps (101).

Chemical feed systems (101) are in fluid contact with the chemical (reagents) for the generation of chlorine dioxide (non-limiting examples $NaClO_2$, $NaOCl$, and $HCl$) and the injection manifold (201). The injection manifold (201) is in fluid contact with the reaction chamber (301). The dilute aqueous solution of chlorine dioxide from the reaction chamber (301) is sent to the application.

Prior art methods and devices for producing chlorine dioxide provide limited variability in mass flow rate of chlorine dioxide and are best suited for near steady state operations allowing for relatively minor changes in chlorine dioxide output. For example, U.S. Pat. Nos. 6,967,010, 7,407,641, and 7,504,074 disclose methods and apparatus for generating chlorine dioxide using educators. The flow rate of chemicals thru an educator depends on the vacuum created by the educator which in turn is dependent on the fixed size and flow rate thru the educator. Such methods are very limited in chlorine dioxide mass flow rate and are best suited to produce a fixed (targeted) amount of chlorine dioxide. For applications that require variable amounts of chlorine dioxide, methods and devices represented by the prior art references generally supply a fixed amount of chlorine dioxide to a storage tank where it can be pumped using a variable feed rate pump.

In another example like that disclosed in U.S. Pat. No. 7,261,821, chemical metering pumps feed chemicals to a reactor to generate chlorine dioxide at a targeted or predetermined concentration. PLC logic is used to modulate the pumps to achieve the predetermined concentration of chlorine dioxide and efficiency while the mass flow rate of chlorine dioxide is controlled by varying the motive water flow rate thru the reactor wherein the chlorine dioxide is generated. Small changes to the predetermined concentration of chlorine dioxide (set-point) are allowed for based on the measured RCD (residual Chlorine Dioxide) concentration using either manual testing methods or automatic testing methods. Again, the variability of chlorine dioxide mass flow rate is restricted based on the motive water flow rate thru the reactor while trying to sustain a targeted (near steady state) concentration of chlorine dioxide exiting the reactor with only slight real-time variability to the mass flow rate not controlled by the motive water flow rate.

The variability allowed by varying water flow rate is extremely limited. For example, a 1 inch pipe may allow from about 1 to 20 gpm of water with a reasonably accurate control and measure of flow rate. This only allows for up to a 1 to 20 turn-down turn-up ratio, severely limiting the application without changing the size or function of the device. Furthermore in the case of educator based chemical feed systems, it is only practical to operate on the higher range of flow rate as enough vacuum must be created to pull the chemicals into the motive water. Too low a flow will not provide sufficient vacuum to draw the chemicals into the stream of water.

In applications exemplified by hydraulic fracturing, the flow rate of water used in hydraulic fracturing can vary greatly. For example, it is common to observe change in flow rates from about 100 gpm to 3,000 gpm in a matter of minutes. Furthermore, the quality of the source of water can vary greatly providing variances in chlorine dioxide demand from near 0 ppm to 10 ppm. Water is often taken from aquifers, ponds, lakes and rivers. The amount of oxidant demand can vary greatly from source to source, and it is not uncommon to have multiple sources be used in the same hydraulic fracturing operation. Furthermore, treatment of flow-back water comprising iron and other sources of demand can easily provide 20-30 ppm of chlorine dioxide demand, thereby requiring a larger chlorine dioxide generating system.

Having a variable mass flow rate chlorine dioxide generating system combined with the process capabilities provided by the turn-down turn-up logic allows for enhanced application under a wide range of real-time varying conditions while providing for the safe and efficient generation of dilute aqueous solutions of chlorine dioxide.

Comparatively, in these types of applications, prior art chlorine dioxide generating systems generate a relatively fixed concentration of chlorine dioxide (measured as ppm) exiting the generator and store it in a vessel where it is applied at the rate needed as described in the referenced prior art U.S. Pat. No. 7,261,821.

Implementation of the newly disclosed invention eliminates the need for storage of chlorine dioxide and the subsequent feed of the stored solution. The disclosed automated process can vary the concentration and mass flow rate of chlorine dioxide in real-time, thereby meeting the chlorine dioxide requirements over a wide range of conditions that cannot be achieved by the prior art devices, processes or methods.

The invention comprises a process for the safe and efficient generation of dilute aqueous solution of chlorine dioxide and methods for use, while providing variable mass flow rate of chlorine dioxide having a turn-down turn-up ratio of at least 1 to 200, preferably at least 1 to 300, and most preferably at least 1 to 500. The invention comprises a plurality of variable feed rate chemical pumps in fluid contact with an injection manifold flooded with water by a source of motive (flowing) water. The plurality of variable feed rate chemical pumps deliver chemicals for the generation of chlorine dioxide (reagents) such as a source of acidified chlorine and a source of chlorite to produce a dilute aqueous solution of chlorine dioxide. The chlorine dioxide concentration exiting the generator can be monitored using an optical sensor, while process conditions such as ORP and/or chlorine dioxide residual of the treated water and process flow rate are monitored. The PLC is configured to adjust the chemical feed rate of the chemical pumps while controlling the motive water flow rate at a targeted setting to achieve the required mass flow rate of chlorine dioxide exiting the generator to maintain the desired ORP and/or residual chlorine dioxide in the treated process water. In the event where the calculated and/or measured concentration of chlorine dioxide exiting the generator were to exceed a maximum $ClO_2$ set-point programmed into the PLC, the PLC in signal contact with the flow regulating valve controls the regulating valve to increase the flow rate of motive water to achieve a chlorine dioxide concentration of less than the maximum $ClO_2$ set-point exiting the generator.

The measured $ClO_2$ concentration of chlorine dioxide can be determined by measuring the $ClO_2$ using an optical sensor. The calculated $ClO_2$ mass flow rate can be determined by knowing the feed rate of sodium chlorite to the injection manifold, the activity of the sodium chlorite (as $ClO_2^-$), the specific gravity of the sodium chlorite solution, and the flow rate of motive water. For example, 25% $NaClO_2$ solution having a specific gravity of about 1.21 (10.12 lb/gal) is fed at a rate of 84 ml/min to a motive water flow rate of 37 liters/min.

The calculated concentration of chlorine dioxide based on 100% conversion (efficiency) is:

[84 ml/min×1000 (mg/ml)×1.21 (sp.gr.)×0.74 (% $ClO_2$ in $NaClO_2$)×0.25 (% NaClO2 activity)] ÷37 liters/min=508 mg/liter.

The motive water, acidified chlorine, and chlorite anion flow through a reaction chamber and convert at least 80 wt %, more preferably 90 wt %, and most preferably 95 wt % of the chlorite anion to chlorine dioxide before being applied to the application.

In one preferred embodiment the control panel actuates the chemical feed systems only when motive (flowing) water is confirmed using a flow sensor or flow meter and a sufficient period of time is allowed to lapse to ensure at least the injection manifold and reaction zone are flooded with motive water before chemical feed is actuated.

In another preferred embodiment the control panel using turn-down turn-up logic varies the feed rate of the chemical pumps to change the concentration of chlorine dioxide exiting the generator while controlling the flow regulating valve to achieve a targeted motive water flow rate while sustaining a chlorine dioxide concentration of less than or equal to the maximum $ClO_2$ set-point. When higher mass flow rate of chlorine dioxide is required that exceeds the calculated or measured maximum $ClO_2$ set-point, the control panel increases the motive water flow rate, thereby lowering the concentration of chlorine dioxide exiting the generator, then increases the feed rate of the chemical pumps, thereby increasing the concentration of chlorine dioxide exiting the generator as well as the overall mass flow rate of chlorine dioxide.

In another preferred embodiment the control panel using turn-down turn-up logic varies the feed rate of the chemical pumps to vary the concentration of chlorine dioxide exiting the generator while controlling the flow regulating valve to achieve a targeted motive water flow rate while sustaining a chlorine dioxide concentration of greater than or equal to the minimum $ClO_2$ set-point. When a lower mass flow rate of chlorine dioxide is desired, the control panel decreases the motive water flow rate thereby increasing the concentration of chlorine dioxide exiting the generator. In this embodiment, more efficient use of chemicals and faster reactions rates are achieved.

The invention provides an automated process for the safe and efficient generation of a dilute aqueous solution of chlorine dioxide having a variable chlorine dioxide mass flow rate of at least 1 to 200 turn-down turn-up ratio, said aqueous solution is applied to oil and gas applications, the process comprising:

a source of motive water in fluid contact with a variable mass flow rate chlorine dioxide generating system comprising: variable feed rate chemical pumps, chemicals for producing chlorine dioxide, flow meter, flow regulating valve, injection manifold, a reaction zone (reactor), pH sensor for monitoring the reactor effluent pH, and an optional optical sensor for measuring chlorine dioxide concentration exiting the reactor;

a control panel comprising a PLC programmed with turn-down turn-up logic and assigned a minimum $ClO_2$ set-point and a maximum $ClO_2$ set-point, the control panel in signal contact with the variable mass flow rate chlorine dioxide generating system and sensors for monitoring process conditions that influence the required mass flow rate of chlorine dioxide exiting the said chlorine dioxide generating system; the PLC applies turn-down turn-up logic to vary the mass flow rate of chlorine dioxide in the motive water to produce a dilute aqueous solution of chlorine dioxide by: (1) varying the concentration of chlorine dioxide by changing the feed rate of the chlorine dioxide generating system chemical pumps while controlling the motive water flow rate to target a predetermined value, and (2) changing the motive water flow rate to target a new predetermined value followed by changing the chemical feed rate of the chlorine dioxide generating system chemical pumps to vary the concentration of chlorine dioxide;

the variation in mass flow rate of chlorine dioxide is achieved while the concentration of chlorine dioxide exiting the chlorine dioxide generator is controlled between the minimum $ClO_2$ set-point and the maximum $ClO_2$ set-point, and applying the dilute aqueous solution of chlorine dioxide to an oil and gas application.

The invention provides the capability to safely and efficiently generate chlorine dioxide using diluted chemicals while achieving variability in the chlorine dioxide mass flow rate needed for variable demand applications like those experienced in oil and gas applications.

The chemical feed systems are controlled by a control panel. The control panel can adjust the chlorine dioxide production rate based on feed-back and/or feed-forward control. For example, oxidation reduction potential (ORP) and/or amperometric sensors can be used to monitor the water being treated with chlorine dioxide. The feed-back from these sensors can be used to automatically adjust the amount of chlorine dioxide being produced by altering the feed-rate of the chemicals used to generate chlorine dioxide. An example of feed-forward is a device that measures the process flow-rate and provides data to the control panel so that the feed-rate of chlorine dioxide is variable based on flow-rate. Feed-back and feed-forward control can be combined to further optimize chlorine dioxide product rate and feed-rate.

Sensors can also be used to monitor and subsequent allow the control panel to vary the feed-rate of chemicals used to optimize the production of chlorine dioxide. For example, pH monitoring of the chlorine dioxide solution can be used to optimize the feed-rate of an acid source used to produce the acidified chlorine. Other sensors can be used to monitor useful parameters. Non-limiting examples of sensors include: oxidation reduction potential (ORP), amperometric, reagent based automatic titrator, pH, conductivity, temperature, and ion specific probes.

Feed-back control can be used to optimize the production rate and feed-rate of chlorine dioxide. Oxidation reduction potential (ORP) is one non-limiting example of a control parameter that can be used as a feed-back control to optimize the feed-rate of chlorine dioxide. As oxidant demand and/or flow-rate change, the ORP controller can provide feed-back that automatically varies the production rate and feed-rate of chlorine dioxide in order to sustain the desired millivolt potential. Depending on the application, proportional, proportional integral, proportional integral differential, or time based proportional control may be used to optimize the generation and feed-rate of chlorine dioxide.

The invention provides a method for safe and efficient generation of chlorine dioxide for the treatment of water in oil and gas applications comprising oil and gas hydraulic fracturing water, desalination water, produced water, and flow-back water.

Oil and gas hydraulic fracturing water (frac water) is water used to create hydraulic fracturing in a rock layer, as a result of the action of a non-compressible pressurized fluid. The fracturing of the rock layer allows trapped oil and gas to be recovered. Frac water must be treated to kill water-borne bacteria to prevent contamination and subsequent souring of the formation.

Flow-back water is water that is returned to the surface after hydraulic fracturing. Flow-back water is frac water that contains frac chemicals such as surfactants, and formation fluid comprising brine, suspended solids and some oil and gas. One method of treating this water comprises treating with chlorine dioxide to break emulsions often accompanying the flow-back water to liberate oil and precipitate dissolved iron and undesirable organics that stabilize the emulsion.

Produced water is the brine water from a producing well that has the oil and gas separated out. In some instances this water can be treated with chlorine dioxide to precipitate iron and other undesirable metals and organics as well as kill bacteria to prepare the water for either deep well injection or for re-use in hydraulic fracturing operations.

Desalination water comprises fresh water often taken from ponds, streams, lakes and aquifers that is treated to kill bacteria and used for dissolving salts in artificial lift equipment that is exposed to saturated brines down-hole.

Other examples of applications that can benefit from the disclose invention follow.

Cooling water can be once-through or circulated for the use of cooling process equipment such as heat exchangers. Circulated cooling water is often passes across cooling towers, or spray ponds to induce evaporation to lose heat of vaporization.

Chlorine dioxide is an effective biocide for treating water used in "food intervention" for the treatment of a food product or food, and/or food processing systems to killing one or more of the food-borne pathogenic bacteria associated with a food product, such as *Salmonella typhimurium, Salmonella javiana, Campylobacter jejuni, Listeria monocytogenes, Escherichia coli* O157:H7, and the like.

A "food product" or "food" refers to any food or beverage item that may be consumed by humans or mammals. Some non-limiting examples of a "food product" or "food" include the following: meat products including ready-to-eat ("RTE") meat and poultry products, processed meat and poultry products, cooked meat and poultry products, and raw meat and poultry products including beet; pork, and poultry products; fish products including cooked and raw fish, shrimp, and shellfish; produce including whole or cut fruits and vegetables and cooked or raw fruits and vegetables; eggs, and egg-based products.

The "food processing systems" refers to the surfaces of equipment and surroundings used to process food. Food processing systems includes the equipment and building structures used to process, produce, store, wash, move, sanitize, cut, and package consumable food items.

Waste-water can be treated with chlorine dioxide to oxidize odors exemplified by the non-limiting examples hydrogen sulfide and mercaptans, kill microbiological organisms, oxidize organics, and induce coagulation. Waste-water is any source of water that is discarded and is not deemed suitable for discharge to NPDES regulated waterways or for use by mammals for washing or consumption.

What is claimed is:

1. An automated process for the safe and efficient generation of a dilute aqueous solution of chlorine dioxide having a variable chlorine dioxide mass flow rate of at least 1 to 200 turn-down turn-up ratio, said aqueous solution is applied to oil and gas applications, the process comprising:
   a source of motive water in fluid contact with a variable mass flow rate chlorine dioxide generating system comprising: variable feed rate chemical pumps, chemicals for producing chlorine dioxide, flow meter, flow regulating valve, injection manifold, a reaction zone (reactor), pH sensor for monitoring the reactor effluent pH, and an optional optical sensor for measuring chlorine dioxide concentration exiting the reactor;

a control panel comprising a PLC programmed with turn-down turn-up logic and assigned a minimum $ClO_2$ set-point and a maximum $ClO_2$ set-point, the control panel in signal contact with the variable mass flow rate chlorine dioxide generating system and sensors for monitoring process conditions that influence the required mass flow rate of chlorine dioxide exiting the said chlorine dioxide generating system;

the PLC applies turn-down turn-up logic to vary the mass flow rate of chlorine dioxide in the motive water to produce a dilute aqueous solution of chlorine dioxide by: (1) varying the concentration of chlorine dioxide by changing the feed rate of the chlorine dioxide generating system chemical pumps while controlling the motive water flow rate to target a predetermined value, and (2) changing the motive water flow rate to target a new predetermined value followed by changing the chemical feed rate of the chlorine dioxide generating system chemical pumps to vary the concentration of chlorine dioxide;

the variation in mass flow rate of chlorine dioxide is achieved while the concentration of chlorine dioxide exiting the chlorine dioxide generator is controlled between the minimum $ClO_2$ set-point and the maximum $ClO_2$ set-point, and applying the dilute aqueous solution of chlorine dioxide to an oil and gas application.

2. The process of claim 1, wherein the minimum $ClO_2$ set-point is greater than or equal to 100 ppm and the maximum $ClO_2$ set-point is less than or equal to 5000 ppm.

3. The process of claim 2, wherein the minimum $ClO_2$ set-point is greater than or equal to 100 ppm and the maximum $ClO_2$ set-point is less than or equal to 4000 ppm.

4. The process of claim 3, wherein the minimum $ClO_2$ set-point is greater than or equal to 100 ppm and the maximum $ClO_2$ set-point is less than or equal to 3000 ppm.

5. The process of claim 1, wherein the turn-down turn-up ratio is at least 1 to 300.

6. The process of claim 5, wherein the turn-down turn-up ratio is at least 1 to 500.

7. The process of claim 1, wherein the oil and gas application comprises water for use in hydraulic fracturing.

8. The process of claim 1, wherein the oil and gas application comprises flow-back water.

9. The process of claim 1, wherein the oil and gas application comprises produced water.

* * * * *